Figure 1:
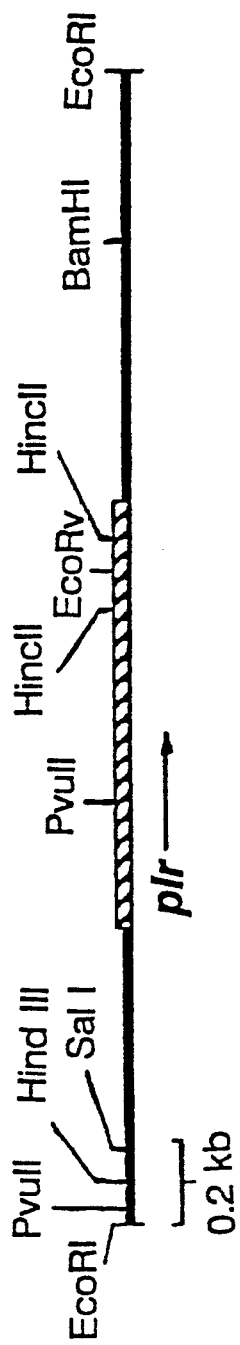

United States Patent [19]

Boyle et al.

[11] Patent Number: 5,328,996
[45] Date of Patent: Jul. 12, 1994

[54] BACTERIAL PLASMIN RECEPTORS AS FIBRINOLYTIC AGENTS

[75] Inventors: Michael D. P. Boyle, Whitehouse, Ohio; Richard Lottenberg, Gainesville, Fla.; Christopher Broder, Rockville, Md.; Gregory Von Mering, Gainesville, Fla.

[73] Assignee: University of Florida Research Foundation, Inc., Gainesville, Fla.

[21] Appl. No.: 928,462

[22] Filed: Aug. 10, 1992

Related U.S. Application Data

[63] Continuation-in-part of Ser. No. 524,411, May 16, 1990, Pat. No. 5,237,050, which is a continuation-in-part of Ser. No. 330,849, Mar. 29, 1989, abandoned.

[51] Int. Cl.$^5$ ............................................. C07H 17/00
[52] U.S. Cl. .................................. 536/23.1; 536/23.7; 424/94.64; 435/172.3; 530/350; 530/388.25; 530/381; 530/825
[58] Field of Search ............................. 536/23.1, 23.7

[56] References Cited

PUBLICATIONS

Lottenberg et al J. of Bact. 174(16):5204, 1992.
Pancholi, V., and V. A. Fischetti (1992) "A Novel Multifunctional Surface Protein (MF6) of group A Streptococci" Abstract of the General Meeting Abstract No. B-252 p. 68.
Blobel, Gunter (1980) "Intracellular protein topogenesis" Proc. Natl. Acad. Sci. USA 77(3):1496–1500.
Ferguson, Michael A. J., and Alan F. Williams (1988) "Cell-Surface Anchoring of Proteins Via Glycosyl–Phosphatidylinositol Structures" Ann. Rev. Biochem. 57:285–320.
Hekman, W. E., D. T. Dennis, and J. A. Miernyk (1990) "Secretion of *Ricinus communis* glyceraldehyde-3-phosphate dehydrogenase by *Escherichia coli*" Molecular Microbiology 4(8):1363–1369.
Allen, Robert W., Kathleen A. Trach, and James A. Hoch (1987) "Identification of the 37-kDa Protein Displaying a Variable Interaction with the Erythroid Cell Membrane as Glyceraldehyde-3-phosphate Dehydrogenase" The Journal of Biological Chemistry 262(2):649–653.
Goudot-Crozel, Veronica, Daniele Caillol, Malek Djabali, and Alan J. Dessein (1989) "The Major Parasite Surface Antigen Associated With Human Resistance to Schistosomiasis is a 37-kD Glyceraldehyde-3-P-Dehydrogenase" J. Exp. Med. 170:2065–2080.
Allen, Robert W., and Beverly A. Hoover (1985) "Characterization of the Processed Form of a Ubiquitous Protein Displaying a Variable Membrane Organization in Erythroid Cells" Blood 65(5):1048–1055.
Michels, Paul A. M., M. Marchand, L. Kohl, S. Albert, R. K. Wierenga, and F. R. Opperdoes (1991) "The cytosolic and glycosomal isoenzymes of glyceraldehyde-3-phosphate dehydrogenase in *Trypanosoma brucei* have a distant evolutionary relationship" Eur. J. Biochem. 198:421–428.
Tso, J. Yun, Xiao-Hong Sun, Teh-hui Kao, Kimberly S. Reece, and Ray Wu (1985) "Isolation and characterization of rat and human glyceraldehyde-3-phosphate dehydrogenase DNAs: genomic complexity and molecular evolution of the gene" Nucleic Acids Research 13(7):2485–2502.

(List continued on next page.)

*Primary Examiner*—Suzanne E. Ziska
*Attorney, Agent, or Firm*—Saliwanchik & Saliwanchik

[57] ABSTRACT

The subject invention concerns novel methods and compositions for thrombolytic therapy. More specifically, a receptor with high affinity for plasmin has been characterized, purified, cloned, and expressed. This receptor can be used in combination therapies where it is administered prior to, concurrently with, or after a plasminogen activator. Also, this receptor can be bound to plasmin and administered to humans or animals in need of fibrinolytic activity. Additionally, the invention pertains to a novel immobilized form of plasmin which advantageously accumulates at the point where antifibrinolytic activity is needed.

2 Claims, 1 Drawing Sheet

OTHER PUBLICATIONS

Lameir, Anne-Marie, A. M. Loiseau, D. A. Kuntz, F. M. Vellieux, Paul A. M. Michels, and F. R. Opperdoes (1991) "They cytosolic and glycosomal glyceraldehyde-3-phosphate dehydrogenase from *Trypanosoma brucei*: Kinetic properties and comparison with homologous enzymes" Eur. J. Biochem. 198:429–435.

Piechaczyk, M., J. M. Blanchard, S. Riaad-El Sabouty, C. Dani, L. Marty, and P. Jeanteur (1984) "Unusual abundance of vertebrate 3-phosphate dehydrogenase pseudogenes" Nature 312(29):469–471.

Alefounder, P. R., and R. N. Perham (1989) "Identification, molecular cloning a sequence analysis of a gene cluster encoding the Class II fructose 1,6-bisphosphate aldolase, 3-phosphoglycerate kinase and a putative second glyceraldehyde 3-phosphate dehydrogenase of *Escherichia coli*" Molecular Microbiology 3(6):723–732.

Holland, Janice P., Laura Labieniec, Candace Swimmer, and Michael J. Holland (1983) "Homologous Nucleotide Sequences at the 5' Termini of Messenger PNAs Synthesized from the Yeast Enolase and Glyceraldehyde-3-phosphate Dehydrogenase Gene Families" The Journal of Biological Chemistry 258(8):5291–5299.

Liotta L. A., R. H. Goldfarb, R. Brundage, G. P. Siegal, V. Terranova, and S. Garbisa (1981) "Effect of Plasminogen Activator (Urokinase), Plasmin, and Thrombin on Glycoprotein and Collagenous Components of Basement Membrane" Cancer Research 41:4629–4636.

Broeseker, Tim A., Michael D. P. Boyle, and Richard Lottenberg (1988) "Characterization of the interaction of human plasmin with its specific receptor on a group A streptococcus" Microbial Pathogenesis 5:19–27.

DesJardin, Lucy E., Michael D. P. Boyle, and Richard Lottenberg (1989) "Group A Streptococci Bind Human Plasmid But Not Other Structurally Related Proteins" Thrombosis Research 55:187–193.

Lottenberg, Richard, Christopher C. Broder, and Michael D. P. Boyle (1987) "Identification of a Specific Receptor for Plasmin on a Group A Streptococcus" Infection and Immunity 55(8):1914–1928.

Bisno, Alan L. (1991) "Group A Streptococcal Infections and Acute Rheumatic Fever" New England Journal of Medicine 325(11):783–793.

Siefring, Gerald E., Jr., and Francis J. Castellino (1976) "Interaction of Streptokinase with Plasminogen: Isolation and Characterization of a Streptokinase Degradation Product" The Journal of Biological Chemistry 251(13):3913–3920.

BACTERIAL PLASMIN RECEPTORS AS FIBRINOLYTIC AGENTS

CROSS-REFERENCE TO A RELATED APPLICATION

This is a continuation-in-part of our co-pending application Ser. No. 07/524,411, filed May 16, 1990; now U.S. Pat. No. 5,237,050 which is a continuation-in-part of application Ser. No. 330,849, filed on Mar. 29, 1989, now abandoned.

BACKGROUND OF THE INVENTION

Ten years ago, the food and drug administration first approved the use of plasminogen activators for thrombolytic therapy. It was originally recommended for the treatment of deep-vein thrombosis and serious pulmonary embolisms. This approach is now also used for treating acute peripheral arterial thrombosis and acute coronary thrombosis and for solubilizing clots in catheters and shunts.

With the development of recombinant DNA technology and the cloning and expression of tissue plasminogen activator (TPA), we have now entered a new age for thrombolytic agents with unique physiological properties and therapeutic promise. The original plasminogen activators that have been used clinically were streptokinase and urokinase. These agents produced in the patients a generalized lytic state which had a variety of side effects that were not directly targeted at solubilizing the fibrin clot. Tissue plasminogen activator, because of its fibrin binding capacity, enhances the selectivity of these agents for fibrin degradation. It is thus being greeted with great fanfare as the new generation of fibrinolytic agents.

Tissue plasminogen activator is not without its potential side effects, and, furthermore, its cost is prohibitive for use in many settings. For example, the V.A. in Gainesville will not authorize tissue plasminogen activator therapy over streptokinase therapy because of its enormous cost. Furthermore, the application of this fibrinolytic therapy to domestic animals or food production animals is limited by the enormous cost.

It is clear to most experts that the wonder drug nature of tissue plasminogen activator has been highly overrated. TPA has been found to have a very short half life in the body. Also, pharmacological doses of tissue plasminogen activator produce a significant bleeding risk for the patient, and in the case of coronary artery thrombosis, re-occlusion of the blood vessel following successful clot lysis occurs in a significant number of patients. The need for an inexpensive, and perhaps even better form of treatment is clearly evident. The use of combination therapies whereby existing compositions and methods are integrally linked in novel ways with new materials and procedures could enhance the effectiveness of plasminogen activators and possibly reduce the amount of plasminogen activator needed to achieve the desired results.

Recently, we have described in our laboratory the presence of a selective, high affinity receptor for human plasmin and other species of plasmin on the surface of certain group A streptococci (Lottenberg, R., C. C. Broder, M. D. P. Boyle [1987] Infect. Immun. 55:1914-1918). Group A streptococci cause pharyngitis and invasive infections such as cellulitis and bacteremia (Bisno, A. L. [1991] New Engl. J. Med. 325:783-793). There has been a recent increase in invasive group A streptococcal infections occurring in healthy individuals. Also, group B streptococci are important pathogens for pregnant women. Staphylococcus aureus, another gram-positive bacteria, is another invasive pathogen for immunocompetent hosts. Effective vaccines to protect against infection by these organisms are not currently available.

The biochemical interactions occurring at cell surfaces between bacterial membranes and their surroundings are complex and not well understood. Certain bacterial surface structures and secreted products have been suggested to contribute to tissue invasion. One of these secreted products, streptokinase, is a plasminogen activator and converts the host zymogen plasminogen to the active protease, plasmin (Siefring, G. E., F. J. Castellino [1976] J. Biol. Chem. 251:3913-3920). Although classically described as the enzyme responsible for fibrin degradation, plasmin is a serine protease with trypsin-like specificity and has activity for a broad range of substrates. Plasmin can degrade several mammalian extracellular matrix proteins, such as fibronectin and laminin, and can enhance collagenase activity (Liotta, L. A., R. H. Goldfarb, R. Brundage [1981] Cancer Res. 41:4629-4636). Therefore, the ability to generate and capture active plasmin may contribute to the invasive propensity of certain streptococcal strains. The interaction of plasmin with group A streptococci has high affinity ($K_d$, $10^{-10}$M) and is specific for plasmin, with no significant binding demonstrated for structurally related proteins (Broeseker, T. A., M. D. P. Boyle, R. Lottenberg [1988] Microb. Pathog. 5:19-27; DesJardin, L. E., M. D. P. Boyle, R. Lottenberg [1989] Thromb. Res. 55:187-193).

As described herein, the plasmin receptor of the subject invention has significant similarity to the glycolytic enzyme glyceraldehyde 3-phosphate dehydrogenase (GAPDH). GAPDH is a key enzyme involved in glucose metabolism and has been the subject of many genetic studies. Multiple copies of GAPDH genes have been identified for mammals, with many described as pseudogenes (Piechaczyk, M., J. M. Blanchard, S. Riaad-El Sabouty, C. Dani, L. Marty, P. Jeanteur [1984] Nature 312:469-471). Multiple GAPDH genes have also been identified for E. coli, Trypanosoma brucei, Saccharomyces cerevisiae, and Drosophila melanogaster (Alefounder, P. R., R. N. Perham [1989] Mol. Microbiol. 3:723-732; Holland, J. P., L. Banieniec, C. Swimmer, M. J. Holland [1983] J. Biol. Chem. 258:5291-5299; Michels, P. A. M., M. Marchand, L. Kohl, S. Allert, R. K. Wierenga, F. R. Opperdoes [1991] Eur. J. Biochem. 198:421-428; Tso, J. Y., X. -H. Sun, R. Wu [1985] Nucleic Acids Res. 17:1251). E. coli and T. brucei each have two GAPDH genes with significant differences in deduced amino acid sequence (Alefounder et al., supra; Michels et al., supra); however, the translated product of the second E. coli GAPDH gene has not been reported. One of the trypanosomal isoenzymes is localized in the glycosome, a specialized metabolic organelle, while the other GAPDH is found in the cytoplasm (Lambier, A. -M., A. M. Loiseau, D. A. Kuntz, F. M. Vellieux, P. A. M. Michels, F. R. Opperdoes [1991] Eur. J. Biochem. 198:429-435).

In addition to its usual intracellular location, GAPDH has been identified on the surface of hematopoietic cells and Schistosoma mansoni, an invasive parasite (Allen, R. W., K. A. Trach, J. A. Hoch [1987] J. Biol. Chem. 262:649-653; Goudot-Crozel, V., D. Caillol, M. Djabali, A. J. Dessein [1989] *J. Exp. Med.* 170:2065-2080). Allen and Hoover ([1985] *Blood* 65:1045-1055) characterized a membrane-associated 37,000-$M_r$ protein expressed by the erythroleukemic cell line K562. Peptide mapping and molecular cloning studies revealed the protein to be homologous to GAPDH (Allen, Trach, and Hoch, supra). A similar finding has been reported for the blood fluke responsible for abdominal schistosomiasis (Goudet-Crozel et al., supra). A 37,000-$M_r$ surface immunogen of *S. mansoni* was characterized by isolating the cDNA encoding the protein. The deduced amino acid sequence had significant homology to that of human GAPDH. Like the recombinant plasmin receptor protein (Plr), neither of these surface proteins had domains corresponding to previously described membrane-anchoring structures (Blobel, G. [1980] *Proc. Natl. Acad. Sci. USA* 77:1496-1500; Ferguson, M. A. J., A. F. Williams [1988] *Annu. Rev. Biochem.* 57:285-320). Interestingly, Hekman et al. (Hekman, W. E., D. T. Dennis, J. A. Miernyk [1990] *Mol. Microbiol.* 4:1363-1369), while studying the expression of recombinant plant GAPDH in *E. coli*, were able to target the protein to the outer membrane by genetically fusing the signal sequence of *E. coli* OmpA to *Ricinus communis* GAPDH. Pancholi et al. have recently reported the isolation of a 39 kD surface protein with GAPDH activity from a group A streptococci (Pancholi, V., V. A. Fischetti [1992] "A Novel Multifunctional Surface Protein (MFG) of group A Streptococci," Abstract No. B-252, Abstracts of the General Meeting 1992:68).

GAPDH from streptococci has not been isolated or characterized, and the relationship of the plasmin receptor to the glycolytically active enzyme remains to be seen.

BRIEF SUMMARY OF THE INVENTION

The subject application pertains to novel compositions and methods for thrombolytic therapy. A receptor for human plasmin has been identified, purified, characterized, cloned and expressed. This receptor has been found to bind with very high affinity to plasmin. When bound to the receptor, plasmin retains its enzymatic activity but is not regulated by $\alpha 2$ antiplasmin.

The isolation and purification of the plasmin receptor protein makes it possible to administer novel compositions and treatments to achieve fibrinolytic activity. Specifically, the receptor protein can be used in combination with existing plasminogen activators in ways which enhance the usefulness of the plasminogen activators while minimizing the negative aspects of these agents. For example, by concurrent or sequential administration of plasminogen activators and the receptor protein it is possible to prolong the effects of the plasminogen activator. The prolongation results from the binding of the receptor molecule to free plasmin produced by the activity of the plasminogen activator. Once the receptor binds with high affinity to the plasmin, the plasmin is no longer inhibited by $\alpha 2$ antiplasmin. In this fashion, the amount of plasminogen activator needed to achieve the desired plasmin activity can be reduced and the disadvantageous effects of the short half life of the plasminogen activator can be minimized.

Immobilized or receptor-bound plasmin can be used in conjunction with the administration of streptokinase, urokinase, tissue plasminogen activator, or other plasminogen activators. The use of our novel plasmin constructs in such a treatment regimen can help to prevent re-occlusion of blood vessels, while the reduced concentration of the plasminogen activator lowers the risk of bleeding.

Furthermore, the receptor molecule can be conjugated to a monoclonal antibody specific for fibrin. In this way, the plasmin can be targeted to the fibrin clot where the fibrinolytic activity is needed. Also, this will help to reduce the amount of plasmin circulating freely in the blood system.

In another embodiment of the subject invention, plasmin can be bound to the receptor before administration to the human or animal in need of thrombolytic activity. Plasmin bound to the receptor will supply the fibrinolytic activity without being rapidly inhibited by $\alpha 2$ antiplasmin.

The subject invention further concerns a process which comprises treating a human or animal in need of fibrinolytic activity with bacteria comprising a selective, high affinity receptor for plasmin, human and otherwise. Exemplified herein is the use of a group A streptococcus receptor which binds human plasmin with, advantageously, a very high affinity and a very slow off-rate. This form of immobilized plasmin has a number of potential applications for thrombolytic therapy, not only in man, but also in animals.

Further aspects of the subject invention pertain to the essentially pure plasmin receptor and the DNA which codes for this protein. The plasmin receptor of the subject invention can be purified from certain bacteria as described below. Also, the receptor can be produced by recombinant techniques using novel clones which express the receptor. The receptor is a $M_r \approx 41,000$ dalton protein that is distinct from the $M_r \approx 47,000$ streptokinase molecule produced by the same bacteria. Unlike the streptokinase, the plasmin receptor protein lacks plasminogen activator activity.

Yet a further aspect of the subject invention pertains to the use of the plasmin receptor as a vaccine to raise an immune response to group A streptococci (GAS) infections and a potentially broad range of infections associated with pathogens expressing GAPDH or GAPDH-like proteins at the cell surfaces.

BRIEF DESCRIPTION OF THE DRAWING

FIG. 1 shows the restriction map of the 2.7-kb EcoRI insert of pRL015. Restriction enzyme recognition sites are indicated. The location of plr is denoted by the hatched box. The arrow indicates the orientation of the open reading frame.

BRIEF DESCRIPTION OF THE SEQUENCES

SEQ ID NO. 1 shows the composite DNA and translated amino acid sequences of the plasmin receptor protein of the subject invention.

SEQ ID NO. 2 is the translated amino acid sequence of the plasmin receptor protein of the subject invention.

DETAILED DESCRIPTION OF THE INVENTION

One of the major problems with plasminogen activator administration is the lytic state that accompanies injection of high concentrations of streptokinase or, to a lesser degree, tissue plasminogen activator. This is due to the generation of plasmin from the plasminogen as the activators circulate throughout the human or animal. Tissue plasminogen activator has a certain affinity for fibrin that allows activation to occur preferentially in the region of the clot.

The purified plasmin receptor of the subject invention can be used in combination with plasminogen activators to produce the desired thrombolytic activity. Advantageously, the use of plasmin receptors can be used to reduce the amount of plasminogen activator needed to achieve the necessary activity. By binding with plasmin generated by plasminogen activators, the receptor is able to greatly prolong the effect of the plasminogen activator. The adverse effects of the short half-life of plasminogen activators are thereby minimized. When the receptor binds to plasmin, the plasmin retains its enzymatic activity but is not inhibited by $\alpha 2$ antiplasmin. Also, the receptor can be conjugated to antibodies which serve to target the enzymatic activity of the plasmin to the blood clot where activity is needed. The use of this combined therapy of plasminogen activator and plasmin receptor facilitates a much more efficient treatment for blood clots. The combined therapy minimizes the deleterious effects which accompany current thrombolytic therapies.

An alternate form of therapy involves the administration of plasmin already bound to the receptor. The receptor may be purified or still associated with the bacteria surface. Plasmin associated with a bacteria circulates freely in the bloodstream until cleared by the reticuloendothelial system and, by virtue of its particle size, it can accumulate in areas where blood clots have formed. Once there, the bacterium-bound enzyme can degrade the fibrin and clear the clot. The bacteria then continue to circulate until the reticuloendothelial system clears the organisms. Our findings that the plasmin receptor is extremely stable and is present on non-viable bacteria makes this approach particularly attractive. It enables micromolar quantities of plasmin to be immobilized on bacteria by adsorption. The bacterial bound plasmin can then be administered intravenously without significant toxicity. The organisms, being non-viable, do not present any risk to the human or animal patient, and the potential for clearance of the organisms following a reasonable half-life in the plasma, would be anticipated by virtue of the normal reticuloendothelial cell function of the human or animal.

Although a pathogenic group A streptococcus is exemplified herein, plasmin receptors have also been identified on a number of other organisms including isolates that, even when viable, are not human pathogens. Other organisms which can be used to practice the subject invention include other groups of streptococci including B, C and G. Also, bovine *Pasteurella haemolytica* as well as *Staphylococcus aureus* microorganisms can be used. These organisms are well-known in the art and are illustrative, but not exhaustive, of the microorganisms which come within the scope of the subject invention.

The major advantage of using plasmin bound to bacteria is the ability to produce a fibrinolytic agent that has selectivity towards the clot, and would not result in a widespread lytic state, all of which can be achieved at a very moderate cost. In addition, the bacterial plasmin receptor has been shown to bind not only to human but other species of plasmin, thereby enabling this approach to thrombolytic therapy to be extended to domestic and food producing animals.

Of particular interest in this regard is a major economic disease in cattle which involves fibrin pneumonia that occurs in cows infected with *Pasteurella haemolytica*. This is a major killer of animals, particularly those suffering from immunosuppression as a consequence of viral infection. This is particularly important in feed lots and under conditions where large numbers of cattle are housed together. There is a great need for the ability to treat the fibrin deposits in the lung, which ultimately suffocate the animal, by aerosol treatment with a plasmin-bacterial complex. In addition, situations for which thrombolytic therapy has been used in human medicine could now be applied to similar situations in animals.

Among the advantages of using bacteria coated with plasmin, are (1) the increased selectivity achieved by immobilizing plasmin in a non-regulatable form on a particle that would circulate with a predictable half-life in the serum of an individual animal; and (2) the low cost, which would then enable the approach to be used for animals as well as man.

We have isolated and analyzed plr, the gene encoding a group A streptococcal plasmin receptor. By screening a λ gt11 expression library with antiplasmin receptor antibodies, we identified a plasmin receptor gene within a 2.7-kb streptococcal DNA fragment. This fragment was subcloned into a low-copy-number plasmid, and the receptor protein was stably expressed in *E. coli* under the control of putative streptococcal promoter elements. The recombinant receptor protein demonstrated immunoreactivity and plasmin-binding activity. We determined the nucleotide sequence for plr and upstream elements of the structural gene. An open reading frame of 1,008 bp was identified. The 40.5% G+C content of plr was slightly higher than the 35 to 39% reported for group A streptococcal chromosomal DNA (Hardie, J. M. [1986] "Genus Streptococcus," pp. 1043–1071, In J. G. Holt et al. (eds.), *Bergey's manual of systematic bacteriology*, Williams & Wilkins, Baltimore). The deduced amino acid sequence was identical for 74 amino acid residues at the N terminus as well as three cyanogen bromide fragments obtained from the native streptococcal protein. The amino acid sequence obtained for the streptococcal receptor protein revealed that the initial methionine residue is cleaved.

The deduced amino acid sequence for the recombinant plasmin receptor protein (Plr) was compared with published sequences for other proteins. Plr exhibits significant similarity to the glycolytic enzyme GAPDH, reported for a number of prokaryotic and eukaryotic organisms. The best match was with *B. subtilis* (56% identical and 73% conserved amino acid residues). GAPDH from streptococci has not been isolated or characterized, and the relationship of the plasmin receptor to the glycolytically active enzyme remains to be defined. However, the extensive amino acid homology and similar hydropathy plots for Plr and *B. subtilis* GAPDH strongly suggest that Plr is a member of the GAPDH family of proteins. Furthermore, preliminary analysis of the recombinant protein revealed that Plr has GAPDH enzymatic activity.

The clones have been transformed into and expressed in *E. coli*. An *Escherichia coli* host containing the clones has been deposited into the permanent collection of the American Type Culture Collection (ATCC), 12301 Parklawn Drive, Rockville, Md. 20852 USA. The culture has been assigned the following accession number:

| Culture | ATCC Designation | Deposit Date |
|---|---|---|
| *Escherichia coli*, chi 6060 (pRL015) | 69415 | December 9, 1993 |

The subject cultures have been deposited under conditions that assure that access to the cultures will be available during the pendency of this patent application to one determined by the Commissioner of Patents and Trademarks to be entitled thereto under 37 CFR 1.14 and 35 USC 122. The deposit is available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposit(s), and in any case, for a period of at least 30 (thirty) years after the date of deposit or for the enforceable life of any patent which may issue disclosing the cultures. The depositor acknowledges the duty to replace the deposits should the depository be unable to furnish a sample when requested, due to the condition of the deposits. All restrictions on the availability to the public of the subject culture deposits will be irrevocably removed upon the granting of a patent disclosing them.

In addition to the plasmin receptor amino acid sequence disclosed herein, the subject invention further comprises equivalent plasmin receptor proteins (and nucleotide sequences coding for equivalent proteins) having the same or similar biological activity of the plasmin receptor exemplified herein. These equivalent proteins may have amino acid homology with the protein disclosed and claimed herein. This amino acid homology will typically be greater than 75%, preferably be greater than 90%, and most preferably be greater than 95%. The amino acid homology will be highest in certain critical regions of the protein which account for biological activity or are involved in the determination of three-dimensional configuration which ultimately is responsible for the biological activity. In this regard, certain amino acid substitutions are acceptable and can be expected if these substitutions are in regions which are not critical to activity or are conservative amino acid substitutions which do not affect the three-dimensional configuration of the molecule. For example, amino acids may be placed in the following classes: nonpolar, uncharged polar, basic, and acidic. Conservative substitutions whereby an amino acid of one class is replaced with another amino acid of the same type fall within the scope of the subject invention so long as the substitution does not materially alter the biological activity of the compound. Table 1 provides a listing of examples of amino acids belonging to each class.

TABLE 1

| Class of Amino Acid | Examples of Amino Acids |
| --- | --- |
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. The critical factor is that these substitutions must not significantly detract from the biological activity of the protein. It has been shown that proteins of identified structure and function may be constructed by changing the amino acid sequence if such changes do not alter the protein secondary structure (Kaiser, E. T. and Kezdy, F. J. [1984] Science 223:249–255). Thus, the subject invention includes mutants of the amino acid sequence depicted herein which do not alter the protein secondary structure, or if the structure is altered, the biological activity is substantially retained.

The genes and proteins according to the subject invention include not only the full length sequences disclosed herein but also fragments of these sequences, or fusion proteins, which retain the characteristic receptor-binding or GAPDH activity of the proteins specifically exemplified herein.

It should be apparent to a person skilled in this art that genes coding for receptor-binding proteins can be identified and obtained through several means. The specific genes may be obtained from a culture depository as described herein. Alternatively, these genes, or portions thereof, may be constructed synthetically, for example, by use of a gene machine. Variations of these genes may be readily constructed using standard techniques for making point mutations. Also, fragments of these genes can be made using commercially available exonucleases or endonucleases according to standard procedures. For example, enzymes such as Bal31 or site-directed mutagenesis can be used to systematically cut off nucleotides from the ends of these genes. Also, genes which code for active fragments may be obtained using a variety of other restriction enzymes. Proteases may be used to directly obtain active fragments of these proteins.

Materials and Methods

Bacterial strains, plasmids, and media. Group A streptococcal strain 64/14 is a M-untypeable clinical isolate that was passaged in mice 14 times (Reis, K. J., M. Yarnall, E. M. Ayoub, M. D. P. Boyle [1984] Scand. J. Immunol. 20:433–439). Escherichia coli Y1090 [$\Delta$lacU169 proA+ $\Delta$lon araD139 strA supF trpC22::Tn10(Tet$^r$)(pMC9)] was used in screening the expression library, and E. coli $\chi$6060 [F' (traD36 proAB lacI$^q$ $\Delta$lacZM15)::Tn5 (Km$^r$)/araD139 $\Delta$(ara leu)7967 $\Delta$lacX74 $\Delta$phoA20 galE galK recA1 rpsE argE(Am) rpoB thi] was used for transformation and gene expression. A low-copy-number plasmid pYA2204 with a replicon derived from pREG153 (a low-copy-number IncW vector derived from the R plasmid R388) was used (Galan, J. E., J. F. Timoney, R. Curtiss III [1988] "Expression and localization of the Streptococcus equi M protein in Escherichia coli and Salmonella typhimurium," p. 34–40, In D. G. Powell, ed., Proceeding of the Fifth International Conference of Equine Infectious Diseases, University Press of Kentucky, Lexington, Ky.). The plr was subcloned into the pUC9 lacZ multiple cloning site of pYA2204.

Streptococci were grown in Todd-Hewitt broth. E. coli Y1090 for $\lambda$ infection was grown in 1% tryptone supplemented with 0.5% yeast extract and 0.4% maltose. E. coli $\chi$6060 was grown in L broth supplemented with kanamycin (50 $\mu$g/ml).

Radioiodination of proteins. Human plasminogen isolated from plasma by chromatography on lysine-Sepharose (Lottenberg, R., F. R. Dolly, C. S. Kitchens [1985] Am. J. Hematol. 19:181–193) and streptococcal protein G (Calbiochem, San Diego, Calif.) were labeled with $^{125}$I (Amersham Corp., Arlington Heights, Ill.) by using a mild lactoperoxidase reaction with Enzymobeads (Bio-Rad, Richmond, Calif.) (McCoy II, E., C. C. Broder, R. Lottenberg [1991] *J. Infect. Dis.* 164:515–521). Plasmin was generated from radiolabeled plasminogen as previously described (Broder, C. C., R. Lottenberg, G. O. von Mering, K. H. Johnston, M. D. P. Boyle [1991] *J. Biol. Chem.* 266:4922–4928).

DNA manipulations. Streptococcal chromosomal DNA was isolated by a modification of the procedure reported by Hudson and Curtiss (Hudson, M. C., R. Curtiss III [1990] *Infect. Immun.* 58:464–470). Streptococci were grown overnight as standing cultures at 37° C. in Todd-Hewitt broth supplemented with 2.2 mM $K_2HPO_4$. Bacterial pellets were treated with lysozyme, mutanolysin, and pronase. The cells were lysed with sodium dodecyl sulfate (SDS). Genomic DNA was further purified by two successive cesium chloride gradient centrifugations. Plasmid DNA was isolated by the alkaline lysis procedure (Birnboim, H. C. [1983] *Methods Enzymol.* 100:243–255) and purified by cesium chloride gradient centrifugation. Restriction enzyme digestions and restrictions with DNA-modifying enzymes were performed according to the manufacturers' recommendations (Bethesda Research Laboratories, Inc., Gaithersburg, Md., and Promega Corp., Madison, Wis.). λ phage were isolated by the plate lysate method (Silhavy, T. J., M. L. Berman, L. W. Enquist [1984] *Experiments with gene fusions*, Cold Spring Harbor Laboratory, Cold Spring Harbor, N.Y.) and then precipitated with polyethylene glycol. DNA was purified by using an anion-exchange resin (Qiagen, Studio City, Calif.). DNA fragments of interest were recovered from agarose gels by using GeneClean (Bio 101, La Jolla, Calif.). Other DNA manipulations were performed essentially as described by Maniatis et al. (Maniatis, T., E. F. Fritsch, J. Sambrook [1982] *Molecular cloning: a laboratory manual*, Cold Spring Harbor Laboratory, Cold Spring Harbor, N.Y.).

Preparation of the λ gt11 library. The streptococcal genomic library was constructed as described by Huynh et al. (Huynh, T. V., R. A. Young, R. W. Davis [1985] "Construction and screening cDNA libraries in λ gt10 and λ gt11," pp. 49–78 In D. M. Glover (ed.), DNA cloning, IRL Press, Oxford). Chromosomal DNA was mechanically sheared to generate fragments approximately 2 to 7 kb in length. The DNA was treated with EcoRI methylase, treated with Klenow fragment of DNA polymerase to generate blunt ends, and ligated with EcoRI linkers. Excess linkers were removed by digestion with a high concentration of EcoRI. The DNA was ligated into EcoRI-generated λ gt11 arms and packaged into λ phage with Packagene (Promega Corp.).

Screening of the streptococcal library. The resulting non-amplified λ gt11 library was diluted in 10 mM Tris-2.5 mM $MgSO_4$-0.01% gelatin-0.1M NaCl, pH 7.5, and used to infect *E. coli* Y1090, yielding a density of 200 to 400 plaques per plate. The infected cells were mixed with 0.45% soft agar, plated on 1.2% L agar supplemented with ampicillin (50 µg/ml), incubated at 42° C. for 3 to 4 hours to induce lysis, and overlaid with nitrocellulose filters impregnated with 10 mM isopropylthiogalactoside (IPTG) to induce the lac promoter. After incubation at 37° C. for approximately 16 hours, the filters were removed, washed, and blocked in 100 mM Tris-300 mM NaCl-5 mM EDTA-0.05% Triton X-100-0.25% gelatin, pH 7.4 (NET-gel). The filters were then incubated with murine antiplasmin receptor antibody (Broder et al. [1991], supra) for approximately 18 hours at room temperature, washed, and then incubated with goat anti-mouse immunoglobulin G (Cappel, Organon Teknika) for 3 to 4 hours. Antigen-antibody complexes on washed filters were detected with $^{125}$I-streptococcal protein G. Autoradiographs were generated by exposing the washed nitrocellulose filters to Kodak XAR-5 film with intensifying screens at −70° C. and then using automated film developing. Immunoreactive plaques were isolated and purified through two additional screenings.

PAGE and protein blotting. SDS-polyacrylamide gel electrophoresis (PAGE) was carried out with a 10% (wt/vol) polyacrylamide separating gel and a 4% (wt/vol) polyacrylamide stacking gel according to the method of Laemmli (Laemmli, U. K. [1970] *Nature* 227:680–685). Gels for Western blotting (immunoblotting) were equilibrated, and separated proteins were transferred by methods described previously (Broder et al. [1991], supra). For studies of plasmin binding, nitrocellulose membranes were blocked for 1 hour at room temperature in NET-gel buffer. The blots were then incubated for 2 hours at room temperature with $^{125}$I-human plasmin to identify plasmin-binding protein bands (Broder et al., supra). The blots were washed in NET-gel and subjected to autoradiography at −70° C.

In vitro transcription-translation. Plasmid-encoded proteins were generated in vitro with a DNA-directed transcription-translation kit (Amersham). Protein products labeled with [$^{35}$S]methionine (specific activity, 1,000 Ci/mmol; Amersham) were subjected to SDS-PAGE and identified by fluorography with sodium salicylate (Chamberlain, J. P. [1979] *Anal. Biochem.* 98:132–135).

Purification of the recombinant streptococcal plasmin receptor protein. *E. coli* χ6060(pRL015) was lysed with a French pressure cell. The resulting material was centrifuged at 10,000×g for 30 minutes, and the supernatant fluids were subjected to ammonium sulfate fractionation. Successive additions of ammonium sulfate were performed at room temperature; the precipitates were removed by centrifugation at 10,000×g for 30 minutes, dialyzed against phosphate-buffered saline, and analyzed by SDS-PAGE and Western blotting. At 55% ammonium sulfate saturation, the recombinant ≈41,000-$M_r$ plasmin receptor protein remained in the supernatant fluid, whereas the majority of *E. coli* proteins precipitated.

DNA sequencing and analysis. DNA sequencing was performed by dideoxy chain termination by using the Sequenase kit (United States Biochemical Corp., Cleveland, Ohio) with α-$^{35}$S-ATP (specific activity>1,000 Ci/mmol; Amersham) by following the instructions of the manufacturer. Sequences were determined by using the universal forward primer supplied with the kit, recessed M13 primers, and sequence-specific oligonucleotides synthesized by the University of Florida Interdisciplinary Center for Biotechnology Research DNA Core Laboratory. Sequences were analyzed with the Genetics Computer Group programs (University of Wisconsin-Madison) (Devereux, J., P. Haeberli, O. Smithies [1984] *Nucleic Acids Res.* 12:387–395).

Amino acid sequencing. Mutanolysin-extracted proteins (Broder et al. [1991], supra) from strain 64/14 were subjected to SDS-PAGE. The proteins were electrotransferred to a polyvinylidene difluoride membrane (Immobilon-P; Millipore Corp., Bedford, Mass.) by using 10 mM 2-(N-morpholino)ethanesulfonic acid (pH 6.0)-20% methanol as the transfer buffer. Protein bands were stained with Coomassie brilliant blue. The ≈41,000-$M_r$ protein band, which had previously been shown to bind plasmin, was excised. Microsequencing by automated Edman chemistry was performed with an Applied Biosystems model 470A gas-phase sequencer with an on-line 12A PTH analyzer (Washington University Protein Chemistry Laboratory). Cyanogen bromide fragmentation of the ≈41,000-$M_r$ protein was performed by immersing the polyvinylidene difluoride membrane-bound protein in 70% formic acid and treating with cyanogen bromide overnight at room temperature. The fragments were separated by SDS-PAGE and transferred to a polyvinylidene difluoride membrane as described above. Four peptides were identified and sequenced at the University of Florida Interdisciplinary Center for Biotechnology Research Protein Chemistry Core Facility by using an Applied Biosystems model 470 sequencer with an on-line PTH analyzer.

Following are examples which illustrate procedures, including the best mode for practicing the invention. These examples should not be construed as limiting. All percentages are by weight and all solvent mixture proportions are by volume unless otherwise noted.

EXAMPLE 1

Human Plasminogen

Plasminogen was prepared from human plasma by chromatography on lysine sepharose (Sigma Chem. Co., St. Louis, Mo. U.S.A.) and molecular sieving chromatography on Sephadex G-100 (Lottenberg, R., F. R. Dolly, C. S. Kitchens [1985] *Am. J. Hematol.* 19:181–193). The purified protein appeared as a single band on a silver stain of an SDS-polyacrylamide gel electrophoresis. A given concentration of isolated plasminogen following activation with streptokinase demonstrated the predicted theoretical amidolytic activity, thereby confirming the purity of the isolated human plasminogen.

EXAMPLE 2

Iodination of Plasminogen

Purified human plasminogen was iodinated by the chloramine T method using Iodobeads (Pierce Chem. Co., Rockford, Ill. U.S.A.) as described in Markwell, M. A. K. (1982) *Anal. Biochem.* 125:427–432. The labeled proteins were separated from free iodine by passage over a G-25 column (PD-10, Pharmacia) and collected in 0.15M Veronal buffered saline, pH 7.4, containing 0.001 M $Mg^{2+}$, 0.00015M $Ca^{2+}$, and 0.1% gelatin(VBS-gel). The labeled proteins were stored in aliquots containing 0.02% sodium azide at −20° C. The specific activity was approximately 25 mCi/mg. The concentration of $^{125}I$-plasminogen was determined using a modification of a previously described enzyme-linked immunosorbent assay (Reis, K. J., G. O. Von Mering, M. A. Karis, E. L. Faulmann, R. Lottenberg, M. D. P. Boyle [1988] *J. Immunol. Methods* 107:273–280). The ELISA could accurately measure 1 ng/ml plasminogen.

EXAMPLE 3

Generation of Plasmin

Plasmin was generated from radiolabeled plasminogen by incubation with urokinase (20 units/ml, Sigma Chemical Co., St. Louis, Mo., U.S.A.) in VBS-gel that contained 0.02M lysine. Conversion was maximal after 30 min at 37° C. The conversion of the single chain zymogen molecule to heavy and light chains was monitored, following reduction, on SDS-PAGE using the method of Laemmli as described previously (Lottenberg, R., C. C. Broder, M. D. P. Boyle [1987] *Infect. Immmun.* 55: 1914–1918). Greater than 95% of plasminogen was consistently converted to plasmin. The specific activity of labeled plasmin was therefore essentially the same as labeled plasminogen.

EXAMPLE 4

Bacteria

The group Aβ-hemolytic streptococcal strain 64 had been previously subjected to mouse passage (Reis, K. J., M. Yarnall, E. M. Ayoub, M. D. P. Boyle [1984] *Scand. J. Immunol.* 20: 433–439). The parent strain (64/P), as well as strains isolated after three (64/3) and fourteen (64/14) passages, were grown in Todd-Hewitt broth (DIFCO, Detroit, Mich.) overnight in phosphate-buffered saline (PBS), pH 7.4, containing 0.05% Tween-20 and 0.02% sodium azide. The bacteria were heat killed at 80° C. for 5 min, a treatment that did not alter their plasmin binding potential, but eliminated the production of soluble plasminogen activators which would interfere with these studies. The suspension was centrifuged, the pellet washed twice with PBS 0.02% sodium azide. Samples were stored at −20° C. The concentration of a bacterial suspension was determined by counting bacterial chains in a Neubauer hemacytometer (Fisher Scientific, Orlando, Fla., U.S.A.)

EXAMPLE 5

Effect of pH and Ionic Strength on Binding

To assess the effect of pH on the bacterium: plasmin (ogen) interaction, 50 μm of labeled plasminogen of plasmin (approximately $2 \times 10^4$ cpm) were added to 1.0 ml of VBS containing 0.05% Tween-20 adjusted to the appropriate pH. After 15 min at room temperature, 50 μm of VBS containing approximately $10^7$ bacteria (strain 64/14) were added and the mixture was incubated at 37° C. for 15 min. The bacterial suspensions were centrifuged at 1000 g for 7 min to separate bacteria from unbound labeled proteins and the pellets were washed twice with 2 ml of VBS at the appropriate pH. The radioactivity associated with the bacterial pellet in duplicate experiments was measured using a Beckman 5500 autogamma counter.

Maximal binding of plasmin to the bacteria was observed between pH 5 and 8 with approximately 60% of counts offered being bound by the group A streptococcus 64/14. In contrast, addition of labeled plasminogen to the bacteria over the entire pH range tested (pH 5–9) resulted in direct binding of less than 10% of offered counts.

To assess the effect of ionic strength on the bacterium:plasmin (ogen) interaction, similar studies were carried out in solutions containing different concentrations of NaCl with 0.05% Tween-20. The bacterial pellets were washed in the appropriate NaCl concentration to remove unbound labeled proteins.

Plasmin binding was dependent on ionic strength and optimal binding occurred between 0.1 and 0.4M NaCl. In this range of salt concentrations, less than 10% of plasminogen bound to bacteria. As the ionic strength was lowered below 0.075M NaCl, significant binding of plasminogen to the bacteria was observed.

EXAMPLE 6

Effect of $Ca^{2+}$ and $Mg^{2+}$ on Binding

Bindings of radiolabeled plasmin to group A streptococci strain 64/14 was studied in the following buffers: (1) VBS-gel containing 0.00015M $Ca^{2+}$ and 0.001M $Mg^{2+}$, or (2) metal free VBS-gel containing 0.15M ethylenediaminetetraacetic acid (EDTA). In each case 400 μl of buffer was added to 100 μl of VBS-gel containing approximately $10^7$ bacteria and 100 μl of VBS-gel containing $3\times10^4$ cpm of radiolabeled plasmin. After incubation at 37° C. for 15 minutes, the mixtures were centrifuged at 1000 g for 7 min to separate bacteria from unbound radiolabel, the pellets were washed twice with 2 ml of the appropriate buffer, and radioactivity associated with the bacterial pellet in duplicate experiments was measured.

The amount of plasmin bound by the bacteria was the same in the presence or absence of divalent cations.

EXAMPLE 7

Inhibition of Binding by Amino Acids

Labeled plasmin (100 μl containing approximately $2\times10^4$ cpm) was added to 200 μl VBS-gel containing varying concentrations of epsilon-aminocaproic acid (EACA), lysine, or arginine, and incubated at 37° C. for 15 min. The pH of each solution was 7.0. One hundred μl of VBS-gel containing $10^7$ bacteria (strain 64/14) were then added and the mixture was incubated at 37° C. for 15 min. The bacterial suspensions were centrifuged at 1000 g for 7 min and washed twice with 2 ml of VBS-gel containing the same concentration of amino acid present during the incubation period. The percent inhibition of binding was calculated for duplicate experiments by comparison with binding in VBS-gel alone.

The ability of EACA, lysine, or arginine to dissociate bound plasmin from the bacteria was examined in the following manner. Labeled plasmin was incubated with $10^7$ bacteria in VBS-gel containing no amino acid at 37° C. for 15 min. The bacteria were pelleted by centrifugation and washed twice with 2 ml on VBS-gel. After determining the radioactivity associated with the bacteria, the pellets were resuspended in solutions of VBS-gel containing varying concentrations of amino acid (pH 7.0) as described above. The mixtures were incubated at 37° C. for 15 min and washed twice with VBS-gel containing the appropriate amino acid concentration. The radioactivity associated with the bacteria in duplicate experiments was again measured and the percentage dissociated was calculated.

Binding of plasmin to the group A streptococcus 64/14 was inhibited by each amino acid in a concentration dependent fashion. Fifty percent inhibition of binding of plasmin to the bacteria was observed at an EACA concentration of 0.15 mM a lysine concentration of 2.0 mM, and an arginine concentration of 25 mM. In similar studies, plasmin was prebound to the group A streptococcus and a concentration dependent elution of bound radiolabel was observed on incubation with EACA, lysine, or arginine. The concentration of amino acid required to elute 50% of the bound plasmin was approximately equivalent to that required to inhibit plasmin binding by 50%.

EXAMPLE 8

Determination of $K_D$ and Receptor Density

Labeled plasmin (25,000 to 250,000 cpm) in 100 μl of VBS-gel was added to $3\times10^6$ bacteria in 300 μl of VBS-gel, pH 7.4, and incubated at 37° C. for 15 min. The bacterial suspensions were centrifuged at 1000 g for 10 min and washed twice with 2 ml of VBS-gel. Experiments were performed in triplicate. Total binding was determined by measuring the radioactivity associated with the bacterial pellet when only labeled plasmin was offered. Non-specific binding was determined by pre-incubation bacteria at 37° C. for 15 min in VBS-gel, pH 7.4, containing unlabeled plasmin at a 100-fold molar excess of the labeled plasmin. Specific binding was calculated by subtracting non-specific binding from total binding for each amount of labeled plasmin offered. The amount of free labeled plasmin was calculated by subtracting the amount of specifically bound labeled plasmin from the total amount of labeled plasmin offered.

The apparent dissociation constant ($K_D$) was determined by two methods. A non-linear least squares analysis of the total counts offered vs. the counts bound fit to the simple Michaelis-Menten equation was performed (Cleland, W. W., [1967] *Adv. Enzymol.* 29: 1-32). The concentration of plasmin was determined specific activity for the labeled plasminogen. Scatchard analysis (Scatchard, G., [1949] *Ann. N.Y. Acad. Sci.* 51: 660-672) of these data was also performed. Counts bound vs. counts bound/counts free was plotted and the slope (representing $-1/K_D$) was determined by linear regression. The x-intercept (counts bound) was converted to moles of plasmin. Receptor density was calculated using this value and the number of bacterial chains offered (derived by hemacytometer chamber counts).

Plasmin which had been bound to and eluted from strain 64/14 by treatment with lysine was also examined in similar binding studies. Eluted plasmin was obtained by incubating 2 ml of stock 10% wet weight/volume bacterial suspension (strain 64/14) with approximately 20 μg of labeled plasmin at room temperature for 45 min. This suspension was centrifuged at 1000 g for 10 min and washed once with 10 ml of VBS-gel, and the radioactivity associated with the bacterial pellet was measured. The pellet was then resuspended in VBS-gel containing 20 mM lysine and incubated at room temperature for 30 min. The suspension was centrifuged and the supernatant recovered. Approximately 90% of the radioactivity originally associated with the bacterial pellet was dissociated by the lysine treatment. The dissociated plasmin in the supernatant was the subjected to gel filtration of a G-25 column to separate lysine from plasmin. Fractions containing plasmin were collected and stored at $-20°$ C.

Non-specific binding demonstrated a linear relationship to counts offered and was less than 5% in all tubes. Analysis of this data by least squares and Scatchard analysis demonstrated a $K_D$ of approximately $5\times10^{-11}$M for the association of plasmin with its receptor on the mouse passaged group A streptococcus strain 64/14. Scatchard analysis of the binding data indicates that there is a single population of plasmin receptors on streptococci, and that strain 64/14 possesses approximately 800 receptors per bacterium.

EXAMPLE 9

Dot-blotting Procedure for the Identification of Plasmin Receptor Activity

Bacterial extracts, chromatography fractions or standards were loaded into the wells of a dot-blotting manifold in 50–200 µl aliquots. Commercially available group C streptokinase was used as a positive plasmin binding control in each assay. All wells were washed twice with 200 µl aliquots of PBS-azide and vacuum drained. All samples were assayed in duplicate. Dot blots were blocked in 5.0 mM sodium diethylbarbiturate, 0.14M NaCl, 0.5% gelatin, 0.15% Tween 20, 0.004% $NaN_3$ pH 7.3. The blots were probed for 3–4 hours at room temperature in the blocking buffer containing 2.0 mM PMSF and $^{125}$I-labeled human plasmin at $3 \times 10^4$ cpm/ml. The probed blots were then washed in 0.01M EDTA pH 7.3, containing 0.5M NaCl 0.25% gelatin, 0.15% Tween 20, and 0.004% $NaN_3$. Autoradiographs were generated by exposing the nitrocellulose blots to Kodak XAR-5 film with an intensifying screen for 15–24 hours at −70° C. followed by automated film developing.

EXAMPLE 10

Polyacrylamide Gel Electrophoresis and Protein Blotting

Gels intended for Western blotting were equilibrated in 25 mM Tris, 0.2M glycine pH 8.0 containing 20% v/v methanol (electroblot buffer) for 25 minutes. Protein blotting, from SDS-PAGE gels, was performed using the 'Trans-Blot SD Semi-Dry' electrophoretic transfer cell (Bio Rad, Richmond, Calif.). Blots were blocked as described for the dot-blot procedure, and probed for 3–4 hours at room temperature with radiolabeled human plasmin in either the presence or absence of 1.0 mM EACA, to identify functionally active protein bands. In studies of antigenic properties of these proteins, blots were probed with rabbit anti-plasmin receptor antibody or anti-group C streptokinase antibody by incubation with 4.3 µg IgG per ml of probing solution (approximately a 1:3000 dilution of antisera) for three hours and probed with $^{125}$I-streptococcal protein G containing $3 \times 10^4$ cpm/ml. For probing with mouse monoclonal antibodies specific for epitopes on group C streptokinase, blots were probed with a 1:100 dilution of the monoclonal antibody stock solution for three hours, followed by probing with goat antibody specific for mouse IgG at 1.0 µg/ml, followed by probing with $^{125}$I-streptococcal protein G containing $3 \times 10^4$ cpm/ml. Blots were then washed with 0.01M EDTA pH 7.3, containing 1.0M NaCl, 0.25% gelatin, 0.15% Tween 20. Autoradiographs were generated by exposing the nitrocellulose blots to Kodak XAR-5 film with an intensifying screen for 15–24 hours at −70° C. followed by automated film developing.

EXAMPLE 11

Mutanolysin Extraction

Generation of cell membrane fragments of streptococcal cell strain 64/14 by mutanolysin generates functional plasmin receptor. Additional purification of receptor is accomplished by affinity chromatography with chemically modified plasmin (Broder et al.). The colony blot immunoassay to monitor the expression of Fc receptors on individual bacterial colonies is described in Yarnall, M., K. J. Reis, E. M. Ayoub, M. D. P. Boyle (1984), "An immunoblotting technique for the detection of bound and secreted bacterial Fc receptors," *J. Microbiol. Meth.* 3:83–93.

This procedure is a modification of the method described by Yarnall, M. and M. D. P. Boyle (1986) "Isolation and partial characterization of a type II Fc receptor from a group A streptococcus," *Mol. Cell. Biochem.* 70:57–66. Approximately 1.0 g wet weight of bacteria was suspended in 5.0 ml of 20 mM $KH_2PO_4$, 1.0 mM EDTA, 0.02% $NaN_3$ pH 7.0 containing 2.0 mM PMSF, 10 µg/ml DNAse I and 50 µg/ml mutanolysin. The suspension was vortexed and placed at 37° C. for 4 hours with periodic mixing. Supernatants were collected following centrifugation to remove bacteria and debris. For these studies a commercial preparation of mutanolysin was further purified according to the method described by Siegal et al. (Siegal, J. L., S. F. Hurst, E. S. Liberman, S. E. Coleman, A. S. Bleiweis [1981] "Mutanolysin-induced spheroplasts of *Streptococcus mutans* are true protoplasts," *Infect. Immun.* 31:303–815) to remove contaminating protease.

EXAMPLE 12

Preparation of Immobilized Human Plasmin Affinity Support

Human plasminogen at a concentration of approximately $5.6 \times 10^{-5}$M was activated to plasmin by incubating the sample in the presence of an approximately 60 fold lower molar concentration of urokinase. The reaction was carried out with constant agitation for one hour at 37° C. in a reaction volume of 10 ml of 0.05M Tris, 0.15M NaCl pH 7.4 containing 40 mM lysine. A 50 µl aliquot was removed and analyzed by SDS-PAGE under reduced conditions to determine the extent of conversion of the single chain plasminogen molecule to the two chain plasmin form. The remainder of the reaction mixture was flash frozen, and stored at −70° C. Preparations in which complete conversion of plasminogen to plasmin was observed were then reacted with constant rotation with a 5 fold molar excess of D-valyl-I-phenylalanyl-L-lysine chloromethyl ketone at ambient temperature with constant rotation. The enzymatically inactive plasmin was then concentrated by ammonium sulfate precipitation (4.0 g/10 ml), dialyzed at 4° C. against 0.1M MOPS buffer, pH 7.3, containing 0.02% sodium azide. The dialyzed inactive plasmin was chromatographed on a Superose 6 column (Pharmacia, Piscataway, N.J.) in 0.1M MOPS buffer, pH 7.3.

The chloromethyl ketone blocked plasmin recovered from the molecular sieving column, was immobilized to the activated affinity chromatography support, Affi-Prep 10 (Bio Rad, Richmond, Calif.). This matrix couples in aqueous buffers to primary amino groups in the ligand by means of an N-hydroxysuccinimide ester on the end of a 10 carbon space arm. Approximately 50 mg of inactivated plasmin in 18 ml of 0.1M MOPS buffer, pH 7.3 was incubated with 6.0 ml of the Affi-Prep 10 bead suspension for 15 hours with rotation at 4° C. Following ligand coupling, 100 µl of 1.0M ethanolamine HCl pH 8 was added and the reaction mixture rotated for 1 hour at 4° C. to block any remaining active sites on the Affi-Prep 10 matrix.

EXAMPLE 13

Affinity Purification of Plasmin Receptor

The Affi-Prep 10-Plasmin matrix was placed in an HR 10/10 column attached to a Pharmacia FPLC chromatography system. The column was equilibrated at room temperature in 0.05M $Na_2HPO_4$, 0.15M NaCl, 1.0 mM benzamidine HCl, 0.02% sodium azide pH 7.2 (equilibration buffer). Approximately 1 or 2 ml of supernatant from the mutanolysin extraction of bacterial strain 64/14 was loaded onto the column. The column was then washed with the equilibration buffer until the $OD_{280}$ returned to base line. The column was then eluted with a 50 ml linear gradient of 0.0M-0.1M L-Lysine in equilibration buffer, or eluted in a single step using equilibration buffer containing 0.1M L-Lysine. The absorbance at 280 nm was continuously monitored an 1.0 ml fractions were collected. After each affinity purification procedure the column was washed with 20 ml of 2.0M NaCl, followed by 200 ml of equilibration buffer and stored at 4° C.

EXAMPLE 14

Production of Polyclonal Antibodies to the Extracted Plasmin Receptor in the Mutanolysin Extract of Strain 64/14

Polyclonal antibodies to the $M_r \approx 41,000$ plasmin receptor protein extracted from strain 64/14 by mutanolysin extraction were prepared in both rabbits and mice. Rabbits were immunized with a gel slice from an SDS-polyacrylamide gel containing approximately 200 µg of the plasmin binding protein emulsified in Freund's complete adjuvant. The rabbit was boosted three times at two week intervals with a gel slice containing approximately 125 µg of the protein emulsified in Freund's incomplete adjuvant. The immunogen was prepared by separating the proteins in a mutanolysin extract of strain 64/14 by electrophoresis on 10% SDS-polyacrylamide gels. The gel was stained to identify protein bands. Plasmin binding proteins were identified by transferring the proteins in one lane of the gel to a nitrocellulose membrane and probing with $^{125}$I-labeled human plasmin, as described above.

Polyclonal antibodies to the $M_r \approx 41,000$ dalton plasmin binding protein were also prepared in mice. For these studies the immunogen was separated on 10% SDS-polyacrylamide gels under reducing conditions using a preparative comb with a single sample well. Separated proteins were transferred to nitrocellulose as described above. Functional plasmin binding proteins were identified by probing with $^{125}$I-labeled human plasmin. The remainder of the nitrocellulose sheet was then stained and the position of the 41,000 dalton band was located and aligned with the autoradiographed strip. The marked band on each nitrocellulose sheet was then carefully cut out to avoid any contamination, and divided into four equal fractions containing approximately 500 µg of protein. The strips were then equilibrated in PBS, sonicated to a fine powder, and subsequently mixed with Ribi Adjuvant. Aliquots of this mixture were used to immunize a group of 6-8 week old out-bred female mice as follows. Initially 10 mice were injected intraperitoneally with approximately 50 µg of antigen immobilized on the nitrocellulose membrane mixed with Ribi adjuvant. Two weeks after the initial injection the mice were boosted intraperitoneally with 10 µg of the nitrocellulose-bound antigen mixed with Ribi adjuvant. Four weeks after the initial injection, the mice were boosted intraperitoneally with 10 µg of nitrocellulose-bound antigen mixed with water. Four days after the final boost the mice were sacrificed and ascites fluid collected from each mouse, pooled and used as a source of antibody.

EXAMPLE 15

Solubilization of Plasmin Receptor

A variety of conditions for solubilizing plasmin receptor activity from the group A streptococcal strain 64/14 were compared. These included hot acid, alkaline, and neutral pH extractions, extraction with the detergents TRITON®X-100 with osmotic shock, acetone and TRITON®X-100 extraction, and extractions with the enzymes, lysozyme, trypsin, or mutanolysin. The highest yield of soluble plasmin binding activity was found in mutanolysin extracts.

The size heterogeneity of the soluble plasmin receptor activity in the mutanolysin extract of strain 64/14 was assessed by electrophoresis of a 50 µl aliquot of the extract on a series of parallel reducing or non-reducing SDS-polyacrylamide gels. The majority of the plasmin binding activity was present predominantly in a band with a $M_r$ of approximately 41,000 daltons. One µg of purified group C streptokinase ($M_r$ approx. 48,000 daltons) was electrophoresed as a positive control for plasmin binding. An aliquot of a sham mutanolysin digest, containing all the reactants, except the bacteria, was also analyzed by Western blotting techniques and demonstrated no plasmin binding activity (data not shown).

EXAMPLE 16

Relationship of the Plasmin Receptor to Streptokinase

Although group A streptococcal plasmin receptor is functionally distinct from streptokinase, the release of this secreted plasmin (ogen) activator from strain 64/14, during extraction, would be a possible confusing factor in the isolation and characterization of the surface plasmin receptor.

The binding specificities of the plasmin receptor extracted from strain 64/14 with streptokinase present in the culture fluid of the same culture were compared. There was no plasminogen activator activity associated with any proteins in the extracted plasmin receptor preparation. A plasminogen activator activity at a $M_r \approx 48,000$ was seen in the lane containing the concentrated supernatant from strain 64/14. This protein migrated at a similar molecular weight in this gel system to the reference group C streptokinase protein.

Comparison of the ability of the samples to bind $^{125}$I-labeled human plasmin demonstrate that the $M_r \approx 48,000$ plasminogen activator bands associated with the reference group C streptokinase or the corresponding molecule from the concentrated culture supernatant of strain 64/14 bound the labeled probe. The mutanolysin extracted plasmin receptor displayed a $M_r \approx 41,000$ dalton band capable of binding to human plasmin; however, this molecule lacked any plasminogen activator potential. A minor $M_r \approx 41,000$ dalton band was present in the concentrated culture supernatant of strain 64/14 which also bound $^{125}$I-labeled human plasmin. This band displayed no plasminogen activator activity.

Previous studies have shown that the binding of human plasmin to the bacterial bound plasmin receptor on strain 64/14 could be inhibited in the presence of EACA. The plasmin binding activity of $M_r \approx 41,000$ dalton band present in the mutanolysin extract of strain 64/14 was reduced significantly in the presence of 1.0 mM EACA. Binding of $^{125}$I-labeled human plasmin to the $M_r \approx 41,000$ dalton plasmin binding protein in the concentrated culture supernatant of strain 64/14 was also inhibited by 1.0 mM EACA. By contrast, addition of EACA had no effect on the binding of plasmin to either the $M_r$ 48,000 plasminogen activator protein from strain 64/14 or to the reference group C streptokinase molecule. Taken together these results indicate that the surface plasmin receptor solubilized by treatment of strain 64/14 with mutanolysin, was unrelated to the streptokinase protein secreted by the same organism. In addition, the results demonstrate that low levels of the plasmin receptor are found in bacterial free culture supernatants in which group A strain 64/14 was grown.

The mutanolysin extracted plasmin binding activity was subjected to further purification by affinity chromatography using an enzymatically inactivated plasmin affinity matrix prepared as described above. One ml of the mutanolysin extract of strain 64/14 was applied to the plasmin affinity column matrix in 0.05M Na$_2$HPO$_4$, 0.15M NaCl, 1.0 mM benzamidine HCl, and 0.02% NaN$_3$, pH 7.2. Bound plasmin receptor activity was eluted using a 50 ml linear gradient of 0.0–0.1M L-Lysine in 0.05M Na$_2$HPO$_4$, 0.15M NaCl, 1.0 mM benzamidine HCl, and 0.02% NaN$_3$, pH 7.2. The absorbance at 280 nm was monitored continuously and 1.0 ml fractions were collected. Fractions eluted from the affinity column were assayed for functional activity using a dot blotting procedure and $^{125}$I-labeled plasmin as the probe. The functional plasmin binding activity was found to bind to the immobilized plasmin matrix and could be eluted selectively with lysine. The recovered functional activity from the column corresponded to the eluted protein peak as detected by measuring absorbance at 280 nm. Identical results were obtained when a single concentration of 0.1M L-lysine was used to elute the bound plasmin receptor activity from the plasmin affinity column.

The molecular size and number of eluted proteins was determined by SDS-PAGE followed by silver staining. The functional activity eluted from the immobilized plasmin matrix in three 1.0 ml fractions. The greatest activity was found in the second protein containing fraction. Fifty microliters of this fraction was analyzed by Western blotting and probing with $^{125}$I-labeled human plasmin. The results indicated that a single $M_r \approx 41,000$ dalton protein was affinity purified and that this protein retained fractional plasmin binding activity. This protein corresponded to the activity present in the crude mutanolysin extract indicating that the affinity purification strategy did not result in any modification of the receptor.

Treatment of the affinity purified material with trypsin destroys the ability of the $M_r \approx 41,000$ dalton molecule to bind plasmin and results in the disappearance of this $M_r \approx 41,000$ dalton band on a silver stained SDS-polyacrylamide gel. These results indicate that a functionally active plasmin binding protein can be isolated by affinity chromatography for a mutanolysin extract of the group A streptococcal strain 64/14. The affinity purified protein, like the crude extract, lacked any plasminogen activating potential.

The group A streptococcal plasmin receptor and streptokinase are physicochemically and functionally distinct molecules. The possibility that the two proteins arose from a common precursor and shared at least some antigenic determinants was considered. This possibility was examined using a polyclonal antibody to streptokinase, as well as rabbit and mouse polyclonal antibodies prepared against the plasmin receptor isolated from strain 64/14.

These findings indicate that the plasminogen activator proteins secreted by group A and group C streptococci were antigenically related. By contrast the $M_r \approx 41,000$ plasmin binding protein extracted from the bacteria or present in low concentrations in culture supernatants displayed no antigenic relatedness with streptokinase as detected by the monospecific polyclonal antibody used.

By contrast, the group A plasmin receptor protein solubilized from the 64/14 bacterial surface was totally devoid of any of the antigenic determinants detected by this the polyclonal anti-streptokinase antibody.

EXAMPLE 17

Cloning and Expression of the Streptococcal Plasmin Receptor Gene

Strain 64/14 produces at least two distinct proteins that display the ability to bind human plasmin(ogen). In addition to the $\approx 41,000$-$M_r$ plasmin receptor, these bacteria secrete an $\approx 47,000$-$M_r$ plasminogen activator protein, streptokinase. Previous studies from our laboratory have shown that these two proteins are antigenically and functionally distinct (Broder et al., supra). Consequently, a monospecific polyclonal antiplasmin receptor antibody preparation, rather than plasmin, was used to screen a group A streptococcal $\lambda$ gt11 expression library generated from strain 64/14 chromosomal DNA. Approximately 13,000 recombinant plaques were screened by using a plaque-lift assay as described in Materials and Methods, and three plaques with strong immunoreactivity were identified and designated SPR4, SPR8, and SPR17. After two rounds of plaque purification, protein products from phage lysates of the three clones were collected and analyzed by SDS-PAGE and Western blot analysis. Each positive clone produced an immunoreactive product with an $M_r$ of $\approx 41,000$ not present in control lysates, indicating that the protein product was not fused with $\beta$-galactosidase.

In order to express the streptococcal plasmin receptor protein (Plr) stably i $E.$ $coli$, subcloning with a plasmid vector was carried out. After digestion of the DNA from SPR4 with EcoRI, agarose gel electrophoresis analysis revealed 2.4- and 2.7-kb DNA fragments in addition to the $\lambda$ arms. We attempted to subclone each of the EcoRI fragments into the EcoRI site of the low-copy-number plasmid pYA2204. We were unable to isolate recombinant plasmids that carried the 2.4-kb fragment. However, the 2.7-kb fragment was successfully subcloned, yielding pRL015. When this plasmid was transformed into $E.$ $coli$ $\chi$6060, an $\approx 41,000$-$M_r$ protein that was recognized by the antiplasmin receptor antibody by Western blotting was observed. This protein was not produced by strain $\chi$6060 alone or by $\chi$6060 transformed with the vector alone.

The $\approx 41,000$-$M_r$ protein expressed from pRL015 was also analyzed for the ability to bind plasmin. Lysates of $\chi$6060 (pRL015) were subjected to SDS-PAGE, transferred to a nitrocellulose membrane, and reacted with $^{125}$I-plasmin. Several proteins contained in lysates of $\chi$6060(pRL015) demonstrated the ability to bind plasmin. Control lysates of $\chi$6060 alone and $\chi$6060(pYA2204) also demonstrated similar plasmin-binding protein bands. Therefore, the streptococcal protein was separated from $E.$ $coli$ plasmin-binding proteins in order to determine whether the recombinant protein had plasmin-binding activity. Supernatant fluids from lysates obtained by French pressure cell treatment of χ6060(pYA2204) as a control and χ6060(pRL015) were subjected to ammonium sulfate precipitation as described in Materials and Methods. The supernatant fluids resulting from a 55% ammonium sulfate cut were analyzed by SDS-PAGE and Western blotting. This manipulation resulted in the precipitation of all plasmin-binding proteins in the control lysate, whereas the ≈41,000-$M_r$ protein produced by χ6060(pRL015) remained in the supernatant fluid. This immunoreactive protein demonstrated the ability to bind $^{125}$I-plasmin.

In vitro transcription-translation studies were performed. SDS-PAGE analysis of the protein products revealed that both pYA2204 (the vector) and pRL015 encoded several proteins with $M_r$ of <30,000; however, pRL015 produced a major protein product with an $M_r$ or ≈41,000 not observed for the control. A minor ≈33,000-$M_r$ protein, which may represent degradation of the ≈41,000-$M_r$ protein or an additional streptococcal encoded product was also identified.

EXAMPLE 18

DNA Sequence and Characterization of the Plasmin Receptor Gene

The restriction map of the 2.7-kb EcoRI insert of pRL015 is depicted in FIG. 1. DNA sequence analysis of the ends of the 2.7-kb fragment did not reveal evidence of an open reading frame. Therefore, subclones for sequencing were generated to locate the gene. The 1.7-kb PvuII-EcoRI fragment representing the right side of the DNA insert (FIG. 1) was ligated with pYA2204 which had been digested with SmaI and EcoRI. Sequence analysis of each end of the insert DNA was performed, and an open reading frame to the right of the PvuII site was identified. By using pRL015, synthetic oligonucleotides were used to extend the sequence upstream and downstream of the PvuII site. A 1,008-bp open reading frame that began with ATG and terminated with a TAA codon was revealed. The G+C content for the open reading frame was 40.5%.

N-terminal amino acid sequencing of the ≈41,000-$M_r$ plasmin receptor protein from strain 64/14 was performed, and an unambiguous sequence was obtained for 51 residues. Amino acid sequences were obtained from four peptides ($M_r$s of 3,000 to 16,000) generated by cyanogen bromide treatment of the ≈41,000-$M_r$ protein. The sequence of one of these peptides had identity with the N-terminal sequence and allowed assignment of an additional 23 residues. The deduced amino acid sequence of the open reading frame exhibited complete identity with 74 amino acid residues of the native protein, indicating that valine following the ATG initiation codon represents the N terminus of the receptor protein. The sequences of two additional peptides (13 and 27 residues) were also determined and found to correspond to residues 160 to 173 and 186 to 216, respectively. Thus, 114 of the predicted 335 amino acid residues encoded by plr have been confirmed by amino acid sequencing of the native streptococcal protein.

Several putative regulatory sequences upstream of the structural gene were identified. A potential ribosomal binding sequence was found at position-9 (AAGGAGG). Putative-35 (TTCACA) and -10 (TCTAAT) regions were identified upstream of the ribosomal binding site with a spacer of 19 bp. An additional subclone with the HindIII-BamHI fragment of pRL015 placed in the opposite orientation to the plasmid-encoded promoter expressed the receptor protein in *E. coli*, indicating that the upstream region served as a functional promoter in *E. coli*.

EXAMPLE 19

Sequence Homologies

The deduced amino acid sequence of Plr was compared with deduced amino acid sequences for genes entered in the EMBL (release 26.0) and GenBank (release 67.0) data bases by using the TFASTA program based on the algorithm of Lipman and Pearson (Lipman, D., W. R. Pearson [1985] *Science* 227: 1435–1441). Glyceraldehyde 3-phosphate dehydrogenases (GAPDHs) of bacterial origins (Branlant, G., C. Branlant [1985] *Eur. J. Biochem.* 150: 61–66; Schlaepfer, B. S., W. Portmann, C. Branlant, G. Branlant, H. Zuber [1990] *Nucleic Acids Res.* 18: 6422; Viaene, A., P. Dhaese [1989] *Nucleic Acids Res.* 17: 1251) exhibited the greatest homology with Plr. The gram-positive *Bacillus subtilis* GAPDH demonstrated the highest score. The sequences showed 56% identity and 73% similarity.

Hydropathy plots of Plr and *B. subtilis* GAPDH were determined as described by Kyte and Doolittle (Kyte, J., R. F. Doolittle [1982] *J. Mol. Biol.* 157: 105–132). Plr and *B. subtilis* GAPDH showed similar patterns overall except for differences in the C-terminal portion of the molecules. Common cell wall-spanning and membrane-anchoring motifs have been identified for several gram-positive surface proteins (Fischetti, V. A., V. Pancholi, O. Schneewing [1991] "Common characteristics of the surface proteins from gram-positive cocci, pp. 290–294, In G. M. Dunny et al. (eds.), *Genetics and molecular biologic of streptococci, lactococci, and enterococci*, American Society for Microbiology, Washington, D.C.). However, no similar regions were identified for Plr. No significant amino acid sequence homology between Plr and streptokinase, the other well-characterized plasmin-(ogen)-binding protein, was identified, supporting our previous biochemical and immunological analyses (Broder et al. [1991], supra).

EXAMPLE 20

Bacterial Plasmin Receptors as Thrombolytic Agents

The plasmin receptors described above can be either purified from bacteria or produced by recombinant technology. These receptors bind plasmin with high affinity but the plasmin retains enzymatic activity. Although plasmin is normally inhibited rapidly by α2 antiplasmin, such inhibition occurs more slowly and to a lesser extent when plasmin is bound to the receptor. These characteristics of the receptor and the plasmin bound to the receptor suggest several novel methods for thrombolytic therapy. First, a composition comprising the purified receptor can be administered in combination with the administration of a plasminogen activator. The receptor may be administered concurrently with the administration of the plasminogen activator. Alternatively, the compositions may be administered sequentially. The receptor should be administered before plasmin produced by the activity of the plasminogen activator has been substantially inhibited by α2 antiplasmin. Therefore, for best results the receptor should be administered concurrently with, or shortly before or after, the administration of the plasminogen activator. This procedure has the advantage of decreasing the amount and frequency of administration of the plasminogen activator. Normally, the short half life of TPA necessitates frequent administration of that agent. Also, the administration of TPA or other plasminogen activators can result in substantial amounts of freely circulating plasmin. This situation is most likely to occur with plasminogen activators such as streptokinase, which do not have any particular affinity for fibrin. A reduction in free plasmin is important to minimize the possibility of unwanted bleeding. Also, free plasmin can actually be detrimental to platelet function.

In a further embodiment, the receptor can be bound to plasmin before administration to the human or animal in need of treatment. When the receptor is bound to plasmin the receptor/plasmin complex can then be administered to a human or animal in need of fibrinolytic activity. The plasmin would then supply this activity without being rapidly inhibited by $\alpha 2$ antiplasmin. This procedure also decreases the amount and frequency of administration of the therapeutic agent.

A further advantage of administering plasmin receptor or plasmin bound to a receptor is that the host's plasminogen is not depleted as much as when plasminogen activators alone are administered. When plasminogen activators alone are administered, much of the plasmin is not specifically directed to the desired location and it simply becomes inactivated through the action of $\alpha 2$-antiplasmin. When the plasmin receptor is administered in combination with the plasminogen activator, it is not necessary to use as much activator and, consequently, the host's plasminogen is conserved. Also, administration of the receptor-plasmin complex provides the host with a source of fibrinolytic activity without depleting the host's own plasminogen.

A further embodiment of the subject invention comprises the conjugation of the receptor or a receptor-plasmin complex to an antibody for fibrin. Antibodies to fibrin are known to those skilled in the art and can be easily produced by those skilled in the art. It is a straightforward matter to a person skilled in the art to conjugate the receptor or receptor-plasmin complex to an appropriate anti-fibrin antibody. The resulting conjugate then directs the fibrinolytic activity of the bound plasmin to the specific site where the activity is needed.

An alternative therapeutic procedure comprises the administration of plasmin bound to inactivated bacteria. In this embodiment the receptor remains attached to the bacteria and the plasmin then binds to the essentially immobilized receptor. Heat-treated or otherwise inactivated bacteria can be prepared in a sterile manner. Human plasminogen (pyrogen and microbial organism-free) can be converted to active plasmin using urokinase under conditions previously described (Lottenberg, R., F. R. Dolly, C. S. Kitchens [1985] *Am. J. Hematology* 19: 181-193). Incubation of the bacteria and plasmin to allow complex formation can be followed by washing of the bacteria to remove unbound plasmin. Streptococcal strains non-pathogenic for humans expressing high levels of plasmin receptors provide an example of bacteria which can be used in the novel process disclosed here. Alternative strains of bacteria or other microorganisms, such as fungi, can also be used. Streptococci expressing fibrinogen receptor, in addition to the plasmin receptor, may offer enhanced fibrin specificity in that the fibrinogen receptor binds to fibrin (ogen). For strains of streptococci harboring a fibrinogen binding component, cell membrane fragments containing this region may provide enhanced fibrin specificity. Advantageously, bacteria with associated plasmin may become entrapped by the thrombus. The enzymatic activity of the plasmin would provide for fibrin degradation leading to thrombus dissolution. Clearance of unassociated bacterium-plasmin conjugates by the reticuloendothelial systems would remove the bacteria from circulation.

Anticipated applications of combination therapies or bacterium-plasmin conjugates as thrombolytic agents in clinical practice include intravenous administration for pulmonary thromboembolism, venous thrombosis, acute myocardial infarction, and local infusion for acute arterial thrombosis, and catheter or other intravascular device occlusion. These treatments essentially target the fibrinolytic activity to the specific location where it is needed. Thus, it is not necessary to provide high level systemic dosages. As described above, one preferred embodiment of the invention involves the combined use of the novel receptor-plasmin conjugates with other available treatments. Such a combination can be used to take advantage of the targeted action of the conjugate as well as the more generalized lytic state resulting from the administration of thrombolytic agents. The deleterious side effects normally associated with the thrombolytic agent can be minimized because lower concentrations are needed when they are administered in conjunction with the immobilized plasmin.

An additional aspect of controlling potential hemorrhage accompanying administration of this agent may be the intravenous administration of epsilon-aminocaproic acid (tradename AMICAR) or tranexamic acid. Typical regimens of these anti-fibrinolytic agents would provide plasma levels of the lysine analogs to dissociate the plasmin from the bacteria (Broeseker, T. A., M. D. P. Boyle, R. Lottenberg [1988] "Characterization of the interaction of human plasmin with its specific receptor on a group A streptococcus," *Microbial Pathogenesis* 5:19-27) and enable rapid inactivation of plasmin by its physiological inhibitors $\alpha 2$-antiplasmin and $\alpha 2$-macroglobulin. This will also provide an approach to prepare the patient for emergency surgical procedures (e.g., coronary artery bypass grafting or administration of alternative anti-thrombotic agents (e.g., heparin).

EXAMPLE 21

Vaccines

The novel plasmin receptor described herein can be used advantageously in an immunogenic composition such as a vaccine. Such a composition, when administered to a person or animal, raises antibodies or other immune response which reduces the susceptibility of that human or animal to infection. Specifically, the plasmin receptor of the subject invention can be used to raise an immune response against group A streptococcal infections. Also, the plasmin receptor can be used to raise an immune response against a variety of infective agents which present an immunogenic GAPDH or GAPDH-like protein. Examples of infectious agents for which the plasmin receptor can be used to raise an immune response include, but are not limited to, group A streptococci, group B streptococci, *Schistosoma mansoni*, and *Staphylococcus aureus.*

Immunogenic compositions (such as vaccines) comprising the plasmin receptor, disclosed herein, and variants or fragments thereof having antigenic properties, can be prepared by procedures well known in the art. For example, such compositions can be prepared as injectables, e.g., liquid solutions or suspensions. Solid forms for solution in, or suspension in, a liquid prior to injection also can be prepared. Optionally, the preparation also can be emulsified. The active antigenic ingredient or ingredients can be mixed with excipients which are pharmaceutically acceptable and compatible with the active ingredient. Examples of suitable excipients are water, saline, dextrose, glycerol, ethanol, or the like, and combinations thereof. In addition, if desired, the immunogenic composition can contain minor amounts of auxiliary substances such as wetting or emulsifying agents, pH buffering agents, or adjuvants such as aluminum hydroxide or muramyl dipeptide or variations thereof. Also, cholera toxin subunit B or other agents which stimulate antibody production at mucosal sites can be used. In the case of peptides, coupling to larger molecules such as KLH or tetanus toxoid sometimes enhances immunogenicity. Vaccines are conventionally administered parenterally, by injection, for example, either subcutaneously or intramuscularly. Additional formulations which are suitable for other modes of administration include suppositories and, in some cases, oral formulations. For suppositories, traditional binders and carriers include, for example, polyalkalene glycols or triglycerides. Suppositories can be formed from mixtures containing the active ingredient in the range of about 0.5% to about 10%, preferably about 1 to about 2%. Oral formulations can include such normally employed excipients as, for example, pharmaceutical grades of mannitol, lactose, starch, magnesium stearate, sodium saccharine, cellulose, magnesium carbonate, and the like. These compositions can take the form of solutions, suspensions, tablets, pills, capsules, sustained release formulations or powders and contain from about 10% to about 95% of active ingredient, preferably from about 25% to about 70%.

The compounds can be formulated into the immunogenic composition as neutral or salt forms. Pharmaceutically acceptable salts include the acid addition salts (formed with the free amino groups of the peptide) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The immunogenic compositions are administered in a manner compatible with the dosage formulation, and in such amount as will be therapeutically effective and immunogenic. The quantity to be administered can depend on the subject to be treated and the degree of protection desired. Advantageously, methods known to promote mucosal immunity can be combined with systemic immunity promoters to maximize protection. Also, the plasmin receptors of the subject invention may be combined with carbohydrate antigenic components to enhance the immunogenic response and provide a broader range of protection. The combination of these antigens may be, for example, through chemical coupling. Precise amounts of active ingredient required to be administered depend on the judgment of the practitioner and can be peculiar to each individual. However, suitable dosage ranges are of the order of about several hundred micrograms active ingredient per individual. Suitable regimes for initial administration and booster shots are also variable, but are typified by an initial administration followed in one or two week intervals by a subsequent injection or other administration.

It should be understood that the examples and embodiments described herein are for illustrative purposes only and that various modifications or changes in light thereof will be suggested to persons skilled in the art and are to be included within the spirit and purview of this application and the scope of the appended claims.

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 1125 base pairs
        ( B ) TYPE: nucleic acid
        ( C ) STRANDEDNESS: both
        ( D ) TOPOLOGY: circular ( i i ) MOLECULE TYPE: DNA (genomic)

( i i i ) HYPOTHETICAL: NO ( v ) FRAGMENT TYPE: N-terminal ( v i ) ORIGINAL SOURCE:
        ( A ) ORGANISM: Streptococcus pyogenes
        ( B ) STRAIN: M untypable
        ( C ) INDIVIDUAL ISOLATE: 64/14

( v i i ) IMMEDIATE SOURCE:
        ( B ) CLONE: pRL015

( i x ) FEATURE:
        ( A ) NAME/KEY: CDS
        ( B ) LOCATION: 115..1122

( i x ) FEATURE:
    ( A ) NAME/KEY: matpeptide
    ( B ) LOCATION: 115..1122
    ( C ) IDENTIFICATION METHOD: experimental
    ( D ) OTHER INFORMATION: /codonstart=115
        / function="High-affinity binding of plasmin(ogen)"
        / product="Streptococcal plasmin receptor"
        / evidence=EXPERIMENTAL
        / gene="plr"
        / number=1
        / label=PLR ( x i ) SEQUENCE DESCRIPTION: SEQ ID NO:1:

```
ATAATAGTTC TGTTGAAAGG TTGTTGCAGA TGACTGTAAG TAATCTTTTC ACAATAGGTA         60

GGGAGCATTC CCTCTAATAA TATTCTTTTG ATTTTCATAA GGAGGAAATC ACTA ATG         117
                                                              Met
                                                                1

GTA GTT AAA GTT GGT ATT AAC GGT TTC GGT CGT ATC GGA CGT CTT GCA         165
Val Val Lys Val Gly Ile Asn Gly Phe Gly Arg Ile Gly Arg Leu Ala
         5                  10                  15

TTC CGC CGT ATT CAA AAC ATC GAA GGT GTT GAA GTA ACT CGT ATC AAT         213
Phe Arg Arg Ile Gln Asn Ile Glu Gly Val Glu Val Thr Arg Ile Asn
     20                  25                  30

GAC CTT ACA GAT CCA AAT ATG CTT GCA CAC TTG TTG AAA TAC GAT ACA         261
Asp Leu Thr Asp Pro Asn Met Leu Ala His Leu Leu Lys Tyr Asp Thr
 35                  40                  45

ACT CAA GGT CGT TTT GAT GGA ACA GTT GAA GTT AAA GAA GGT GGA TTT         309
Thr Gln Gly Arg Phe Asp Gly Thr Val Glu Val Lys Glu Gly Gly Phe
 50                  55                  60                  65

GAA GTA AAC GGA AAC TTC ATC AAA GTT TCT GCT GAA CGT GAT CCA GAA         357
Glu Val Asn Gly Asn Phe Ile Lys Val Ser Ala Glu Arg Asp Pro Glu
                 70                  75                  80

AAC ATC GAC TGG GCA ACT GAT GGG GTT GAA ATC GTT CTT GAA GCA ACT         405
Asn Ile Asp Trp Ala Thr Asp Gly Val Glu Ile Val Leu Glu Ala Thr
             85                  90                  95

GGT TTC TTT GCT AAA AAA GAA GCA GCT GAA AAA CAC TTA CAT GCT AAC         453
Gly Phe Phe Ala Lys Lys Glu Ala Ala Glu Lys His Leu His Ala Asn
         100                 105                 110

GGT GCT AAA AAA GTT GTT ATC ACA GCT CCT GGT GGA AAC GAT GTT AAA         501
Gly Ala Lys Lys Val Val Ile Thr Ala Pro Gly Gly Asn Asp Val Lys
     115                 120                 125

ACA GTT GTT TTC AAC ACT AAC CAC GAC ATT CTT GAC GGT ACT GAA ACA         549
Thr Val Val Phe Asn Thr Asn His Asp Ile Leu Asp Gly Thr Glu Thr
130                 135                 140                 145

GTT ATC TCA GGT GCT TCA TGT ACT ACA AAC TGT TTA GCT CCT ATG GCT         597
Val Ile Ser Gly Ala Ser Cys Thr Thr Asn Cys Leu Ala Pro Met Ala
                 150                 155                 160

AAA GCT CTT CAC GAT GCA TTC GGT ATT CAA AAA GGT CTT ATG ACT ACA         645
Lys Ala Leu His Asp Ala Phe Gly Ile Gln Lys Gly Leu Met Thr Thr
             165                 170                 175

ATC CAC GCT TAC ACT GGT GAC CAA ATG ATC CTT GAC GGA CCA CAC CGT         693
Ile His Ala Tyr Thr Gly Asp Gln Met Ile Leu Asp Gly Pro His Arg
         180                 185                 190

GGT GGT GAC CTT CGT CGT GCA CGC GCT GGT GCT GCA AAC ATC GTT CCT         741
Gly Gly Asp Leu Arg Arg Ala Arg Ala Gly Ala Ala Asn Ile Val Pro
     195                 200                 205

AAC TCA ACT GGT GCT GCT AAA GCT ATC GGT CTT GTT ATC CCA GAA CTT         789
Asn Ser Thr Gly Ala Ala Lys Ala Ile Gly Leu Val Ile Pro Glu Leu
210                 215                 220                 225

AAC GGT AAA CTT GAC GGT GCT GCA CAA CGT GTT CCT GTT CCA ACT GGA         837
Asn Gly Lys Leu Asp Gly Ala Ala Gln Arg Val Pro Val Pro Thr Gly
                 230                 235                 240
```

| | | | | | | | | | | | | | | | |
|---|---|---|---|---|---|---|---|---|---|---|---|---|---|---|---|
|TCA|GTA|ACT|GAG|TTG|GTT|GTA|ACT|CTT|GAC|AAA|AAC|GTT|TCT|GTT|GAC|
|Ser|Val|Thr|Glu 245|Leu|Val|Val|Thr|Leu 250|Asp|Lys|Asn|Val|Ser 255|Val|Asp|

885

|GAA|ATC|AAC|TCT|GCT|ATG|AAA|GCT|GCT|TCA|AAC|GAT|AGC|TTC|GGT|TAC|
|---|---|---|---|---|---|---|---|---|---|---|---|---|---|---|---|
|Glu|Ile|Asn 260|Ser|Ala|Met|Lys|Ala|Ala 265|Ser|Asn|Asp|Ser 270|Phe|Gly|Tyr|

933

|ACT|GAA|GAT|CCA|ATC|GTT|TCT|TCA|GAT|ATC|GTA|GGC|GTA|TCA|TAC|GGT|
|---|---|---|---|---|---|---|---|---|---|---|---|---|---|---|---|
|Thr|Glu 275|Asp|Pro|Ile|Val|Ser|Ser 280|Asp|Ile|Val|Gly 285|Val|Ser|Tyr|Gly|

981

|TCA|TTG|TTT|GAC|GCA|ACT|CAA|ACT|AAA|GTA|ATG|GAA|GTT|GAC|GGA|TCA|
|---|---|---|---|---|---|---|---|---|---|---|---|---|---|---|---|
|Ser 290|Leu|Phe|Asp|Ala|Thr 295|Gln|Thr|Lys|Val|Met 300|Glu|Val|Asp|Gly|Ser 305|

1029

|CAA|TTG|GTT|AAA|GTT|GTA|TCA|TGG|TAT|GAC|AAC|GAA|ATG|TCT|TAC|ACT|
|---|---|---|---|---|---|---|---|---|---|---|---|---|---|---|---|
|Gln|Leu|Val|Lys|Val 310|Val|Ser|Trp|Tyr|Asp 315|Asn|Glu|Met|Ser|Tyr 320|Thr|

1077

|GCT|CAA|CTT|GTA|CGT|ACT|CTT|GAG|TAC|TTC|GCA|AAA|ATT|GCT|AAA|
|---|---|---|---|---|---|---|---|---|---|---|---|---|---|---|
|Ala|Gln|Leu|Val 325|Arg|Thr|Leu|Glu|Tyr 330|Phe|Ala|Lys|Ile|Ala 335|Lys|

1122

TAA                                                                      1125

( 2 ) INFORMATION FOR SEQ ID NO:2:

( i ) SEQUENCE CHARACTERISTICS:
( A ) LENGTH: 336 amino acids
( B ) TYPE: amino acid
( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
|Met 1|Val|Val|Lys|Val 5|Gly|Ile|Asn|Gly|Phe 10|Gly|Arg|Ile|Gly|Arg 15|Leu|
|Ala|Phe|Arg|Arg 20|Ile|Gln|Asn|Ile|Glu 25|Gly|Val|Glu|Val|Thr 30|Arg|Ile|
|Asn|Asp|Leu 35|Thr|Asp|Pro|Asn|Met 40|Leu|Ala|His|Leu|Leu 45|Lys|Tyr|Asp|
|Thr|Thr 50|Gln|Gly|Arg|Phe|Asp 55|Gly|Thr|Val|Glu|Val 60|Lys|Glu|Gly|Gly|
|Phe 65|Glu|Val|Asn|Gly|Asn 70|Phe|Ile|Lys|Val|Ser 75|Ala|Glu|Arg|Asp|Pro 80|
|Glu|Asn|Ile|Asp|Trp 85|Ala|Thr|Asp|Gly|Val 90|Glu|Ile|Val|Leu|Glu 95|Ala|
|Thr|Gly|Phe|Phe 100|Ala|Lys|Lys|Glu|Ala 105|Ala|Glu|Lys|His|Leu 110|His|Ala|
|Asn|Gly|Ala 115|Lys|Lys|Val|Val|Ile 120|Thr|Ala|Pro|Gly|Gly 125|Asn|Asp|Val|
|Lys|Thr 130|Val|Val|Phe|Asn|Thr 135|Asn|His|Asp|Ile|Leu 140|Asp|Gly|Thr|Glu|
|Thr 145|Val|Ile|Ser|Gly|Ala 150|Ser|Cys|Thr|Thr|Asn 155|Cys|Leu|Ala|Pro|Met 160|
|Ala|Lys|Ala|Leu|His 165|Asp|Ala|Phe|Gly|Ile 170|Gln|Lys|Gly|Leu|Met 175|Thr|
|Thr|Ile|His|Ala 180|Tyr|Thr|Gly|Asp|Gln 185|Met|Ile|Leu|Asp|Gly 190|Pro|His|
|Arg|Gly|Gly 195|Asp|Leu|Arg|Arg|Ala 200|Arg|Ala|Gly|Ala|Ala 205|Asn|Ile|Val|
|Pro|Asn 210|Ser|Thr|Gly|Ala|Ala 215|Lys|Ala|Ile|Gly|Leu 220|Val|Ile|Pro|Glu|
|Leu|Asn|Gly|Lys|Leu|Asp|Gly|Ala|Ala|Gln|Arg|Val|Pro|Val|Pro|Thr|

|     |     |     |     |     |     |     |     |     |     |     |     |     |     |     |     |
|-----|-----|-----|-----|-----|-----|-----|-----|-----|-----|-----|-----|-----|-----|-----|-----|
| 225 |     |     |     |     | 230 |     |     |     |     | 235 |     |     |     |     | 240 |
| Gly | Ser | Val | Thr | Glu<br>245 | Leu | Val | Val | Thr | Leu<br>250 | Asp | Lys | Asn | Val | Ser<br>255 | Val |
| Asp | Glu | Ile | Asn<br>260 | Ser | Ala | Met | Lys | Ala<br>265 | Ala | Ser | Asn | Asp | Ser<br>270 | Phe | Gly |
| Tyr | Thr | Glu<br>275 | Asp | Pro | Ile | Val | Ser<br>280 | Ser | Asp | Ile | Val | Gly<br>285 | Val | Ser | Tyr |
| Gly | Ser<br>290 | Leu | Phe | Asp | Ala | Thr<br>295 | Gln | Thr | Lys | Val | Met<br>300 | Glu | Val | Asp | Gly |
| Ser<br>305 | Gln | Leu | Val | Lys | Val<br>310 | Val | Ser | Trp | Tyr | Asp<br>315 | Asn | Glu | Met | Ser | Tyr<br>320 |
| Thr | Ala | Gln | Leu | Val<br>325 | Arg | Thr | Leu | Glu | Tyr<br>330 | Phe | Ala | Lys | Ile | Ala<br>335 | Lys |

We claim:

1. Isolated DNA, encoding a plasmin receptor having a molecular weight of about 41 kD, said plasmin receptor consisting essentially of the amino acid sequence set forth in SEQ. ID NO. 2.

2. The isolated DNA according to claim 1, said DNA consisting essentially of the sequence set forth in SEQ. ID NO. 1.

* * * * *

UNITED STATES PATENT AND TRADEMARK OFFICE
CERTIFICATE OF CORRECTION

PATENT NO. : 5,328,996
DATED : July 12, 1994
INVENTOR(S) : Boyle, et. al.

It is certified that error appears in the above-indentified patent and that said Letters Patent is hereby corrected as shown below:

Column 12, line 36: Delete "$\mu m$" and insert --$\mu l$--.

Column 12, line 40: Delete "$\mu m$" and insert --$\mu l$--.

Column 16, lines 41-42: Delete "D-valyl-I-phenylalanyl-L-lysine" and insert --D-valyl-L-phenylalanyl-L-lysine--.

Column 20, line 44: Delete "stably i" and insert --stably in--.

Column 22, line 32: Delete "Schneewing" and insert --Schneewind--.

Signed and Sealed this

Twentieth Day of September, 1994

Attest:

BRUCE LEHMAN

*Attesting Officer*    *Commissioner of Patents and Trademarks*